(12) United States Patent
Wu

(10) Patent No.: US 9,528,954 B2
(45) Date of Patent: Dec. 27, 2016

(54) BIOSENSOR CHIP HAVING PRECISE COUNT FUNCTION AND METHOD OF SENSING AMOUNT OF CELLS

(71) Applicant: KUN SHAN UNIVERSITY, Tainan (TW)

(72) Inventor: Hung-Wei Wu, Tainan (TW)

(73) Assignee: KUN SHAN UNIVERSITY, Tainan (TW)

(*) Notice: Subject to any disclaimer, the term of this patent is extended or adjusted under 35 U.S.C. 154(b) by 238 days.

(21) Appl. No.: 14/458,978

(22) Filed: Aug. 13, 2014

(65) Prior Publication Data
US 2015/0267239 A1    Sep. 24, 2015

(30) Foreign Application Priority Data
Mar. 18, 2014  (TW) .............................. 103110187 A (51) Int. Cl.
| G01N 33/48 | (2006.01) |
| G01N 33/50 | (2006.01) |
| G01N 27/02 | (2006.01) |
| G06F 19/12 | (2011.01) |
| G06F 19/18 | (2011.01) |
| G06F 19/16 | (2011.01) |
| G01N 22/00 | (2006.01) |

(52) U.S. Cl.
CPC .............. *G01N 27/02* (2013.01); *G01N 22/00* (2013.01); *G06F 19/12* (2013.01); *G06F 19/16* (2013.01); *G06F 19/18* (2013.01)

(58) Field of Classification Search
None
See application file for complete search history.

(56) References Cited

U.S. PATENT DOCUMENTS

2003/0039455 A1* 2/2003 Ouchi ................. G02B 6/1221
                                                                 385/88

OTHER PUBLICATIONS

Yang et al. Characteristics of coplanar waveguide on lithium niobate crystals as a microwave substrate. Journal of Applied Physics, vol. 101, 2007, article 014101, pp. 1-5.*
Yang et al. Distinguishing the viability of a single yeast cell with an ultra-sensitive radio frequency sensor. Lab on a Chip, 2010, vol. 10, pp. 553-555.*
"Scattering parameters," https://en.wikipedia.org/wiki/Scattering_parameters, Contents 3: Two-Port S-Parameters, first published on Aug. 11, 2013.

* cited by examiner

*Primary Examiner* — Russell S Negin
(74) *Attorney, Agent, or Firm* — CKC & Partners Co., Ltd.

(57) ABSTRACT

Disclosure is a biosensor chip having precise count function comprising: a substrate, a plurality of ground wire waveguide layers, a signal waveguide layer and a protective layer. Wherein, the plurality of ground wire waveguide layers are located on two sides of the substrate, the signal waveguide layer is located on the substrate and between the plurality of ground wire waveguide layers, wherein the signal waveguide layer has a recess which forms a cell sensing region; and the protective layer covers a portion of the ground wire waveguide layers and a portion of the signal waveguide layer to expose the recess.

6 Claims, 8 Drawing Sheets

BIOSENSOR CHIP HAVING PRECISE COUNT FUNCTION AND METHOD OF SENSING AMOUNT OF CELLS

CROSS-REFERENCE TO RELATED APPLICATION

This application claims the benefit of Taiwan Patent Application No. 103110187, filed on Mar. 18, 2014, in the Taiwan Intellectual Property Office, the disclosure of which is incorporated herein its entirety by reference.

BACKGROUND OF THE INVENTION

1. Field of the Invention

The present invention generally relates to a biosensor chip and a method of sensing amount of cells, in particular with respect to a biosensor chip having precise count function and a sensing method.

2. Description of the Related Art

The purpose of cancer screening is aimed to detect cancer before the symptom is occurred. At present, the screening methods include medical imaging and indicator analysis of blood, urine . . . etc. Although medical imaging is of higher sensitivity towards cancer screening, it is still not suitable for detecting tumors of smaller than 0.1 cm (about 105 tumor cells). The conventional biomedical science indicators, such as prostate-specific antigen (PSA), cancer antigen 125 (CA-125), alpha-fetoprotein (AFP), human chorionic gonadotropin (HCG) and DR70, have been used as cancer marker on clinical detection; nonetheless, applying those detection methods to cancer screening still has various limitations, such as indirect determination on tumor cells counting, time-consuming blood sample separation or precision is interfered due to physical conditions (e.g. infection, inflammation or menstruation) and so on.

Currently, many biologists focus on research into cancer cells, but numerous tumor cells (and/or cancer stem cells) are characterized of un-differentiated, resulting that is hard to distinguish from the differences. Therefore, as far as the biologists are concerned, the dielectric property of cell is regarded as one of significant tools which can be applied to count amount of cells. The known methods, however, are invasive and time-consuming, and cells necessitate to be separated from the growth surface, took out of cell culture vessel and stained before counted. As a result, how to reach purposes of low cost, high quality, low power-consumption and being able to detect less biological molecules becomes a problem of development of biosensor.

SUMMARY OF THE INVENTION

In view of the aforementioned problems of the conventional art, one purpose of the present invention is to provide a biosensor chip having precise count function and a method of sensing amount of cells to detect amount of cells precisely.

According to goal of the present invention, it provides a biosensor chip having precise count function comprising: a substrate; a plurality of ground wire waveguide layers located on two sides of the substrate; a signal waveguide layer located on the substrate and between the plurality of ground wire waveguide layers, wherein the signal waveguide layer has a recess which forms a cell sensing region; and a protective layer covering a portion of the ground wire waveguide layers and a portion of the signal waveguide layer to expose the recess.

The aforementioned plurality of ground wire waveguide layers and the signal waveguide layer may be formed by stacking a first metal layer and a second metal layer. Wherein, the first metal layer and the second metal layer may be formed of Ni, Cr, Ti or Au, respectively.

The aforementioned substrate may be a glass substrate.

The aforementioned protective layer may be formed of SU-8 photoresist.

Operating frequency band of the aforementioned biosensor chip having precise count function may be between 1 GHz and 40 GHz.

In addition, the present invention further provides a method of sensing cell using the aforementioned biosensor chip having precise count function, wherein the cell may be placed in a culture medium, and the method of sensing cell may comprise: measuring the biosensor chip to obtain a cell scattering parameter $$\begin{bmatrix} S_{11} & S_{12} \\ S_{21} & S_{22} \end{bmatrix}_{cell};$$

and amount of the cells is obtained from the cell scattering parameter $$\begin{bmatrix} S_{11} & S_{12} \\ S_{21} & S_{22} \end{bmatrix}_{cell}.$$

wherein the cell scattering parameter may be satisfied with following relations in order to remove the microwave parasitic effect of the culture medium and the substrate effectively:

$$\begin{bmatrix} S_{11} & S_{12} \\ S_{21} & S_{22} \end{bmatrix}_{cell} = \begin{bmatrix} S_{11} & S_{12} \\ S_{21} & S_{22} \end{bmatrix}_{loaded} - \begin{bmatrix} S_{11} & S_{12} \\ S_{21} & S_{22} \end{bmatrix}_{medium} - \begin{bmatrix} S_{11} & S_{12} \\ S_{21} & S_{22} \end{bmatrix}_{unloaded},$$

wherein $\begin{bmatrix} S_{11} & S_{12} \\ S_{21} & S_{22} \end{bmatrix}_{loaded}$ is a loaded scattering parameter obtained by measuring the biosensor chip injecting the cell and the culture medium;

$$\begin{bmatrix} S_{11} & S_{12} \\ S_{21} & S_{22} \end{bmatrix}_{medium}$$

is a medium scattering parameter obtained by measuring the biosensor chip only injecting the culture medium; and $$\begin{bmatrix} S_{11} & S_{12} \\ S_{21} & S_{22} \end{bmatrix}_{unloaded}$$

is an unloaded scattering parameter obtained by measuring the biosensor chip not injecting the cell and the culture medium.

The aforementioned method of sensing cell may further obtain a propagation constant $\gamma(f)=\alpha(f)+j\beta(f)$ from the cell scattering parameter $$\begin{bmatrix} S_{11} & S_{12} \\ S_{21} & S_{22} \end{bmatrix}_{cell}, \text{wherein}$$

$$\alpha(f) = 8.686 \cdot \left[ -\frac{1}{L} \text{Re} \left\{ \ln \left[ \frac{1 - S_{11}^2 + S_{21}^2}{2S_{21}} \pm \left[ \frac{(S_{11}^2 - S_{21}^2 + 1)^2 - (2S_{11})^2}{(2S_{21})^2} \right]^{1/2} \right]^{-1} \right\} \right];$$

$$\beta(f) = -\frac{1}{L} \text{Im} \left\{ \ln \left[ \frac{1 - S_{11}^2 + S_{21}^2}{2S_{21}} \pm \left[ \frac{(S_{11}^2 - S_{21}^2 + 1)^2 - (2S_{11})^2}{(2S_{21})^2} \right]^{1/2} \right]^{-1} \right\} = \frac{2\pi \cdot f \sqrt{\varepsilon_{\mathit{eff}}(f)}}{c},$$

and wherein L is a length of the signal waveguide layer; $\in_{\mathit{eff}}(f)$ is an effective dielectric constant; f is a frequency.

The aforementioned method of sensing cell may further obtain a characteristic impedance $$Z_0(f) = \frac{30\pi}{\sqrt{\varepsilon_{\mathit{eff}}(f)}} \frac{K(k_0')}{K(k_0)}$$

from the effective dielectric constant $\in_{\mathit{eff}}(f)$, and wherein K(x) is an elliptical integral of a first kind;

$$k_0 = \frac{S}{S + 2G}; k_1 = \frac{\sinh(\pi S/4h)}{\sinh(\pi(S + 2G)/4h)}; k_i' = \sqrt{1 - k_i^2} \quad (i = 0, 1);$$

s is a width of the signal waveguide layer; G is an interval between the ground wire waveguide layer and the signal waveguide layer; and h is a thickness of the substrate.

The aforementioned method of sensing cell may further obtain an equivalent resistance $R(f)_{cell}$ and an equivalent capacitance $C(f)_{cell}$ of the cell from relations of $\gamma(f) \times Z_0(f) = R(f) + j\omega \cdot L(f)$ and $\gamma(f)/Z_0(f) = G(f) + j\omega \cdot C(f)$, wherein R(f) is a resistance, L(f) is an inductance, G(f) is an conductance, C(f) is a capacitance and ω is an angular frequency.

In accordance with the preceding description, according to a biosensor chip having precise count function and a method of sensing amount of cells of the present invention, there may have one or more advantages as follows:

(1) The biosensor chip having precise count function is capable of detecting amount of cells precisely by a cell sensing region formed of a recess of the signal waveguide layer.

(2) The biosensor chip having precise count function is capable of covering frequency band between 1 GHz and 40 GHz, and comparing with specific resonant peak measured by the conventional sensing chip, the biosensor chip is not only of higher sensitivity, but also has a wider frequency band and a continuous frequency response.

(3) The biosensor chip having precise count function is capable of removing the microwave parasitic effect of the culture medium and the substrate effectively by the preceding scattering parameter relations so as to obtain a more precise amount of cells.

Hereinafter, embodiments of the present invention will be described in detail with reference to the accompanying drawings so that those skilled in the art to which the present invention pertains can realize the present invention.

DETAILED DESCRIPTION OF THE PREFERRED EMBODIMENTS

As those skilled in the art would realize, the described embodiments may be modified in various different ways, all without departing from the spirit or scope of the present invention. The drawings and description are to be regarded as illustrative in nature and not restrictive. Like reference numerals designate like elements throughout the specification.

Figure 1:
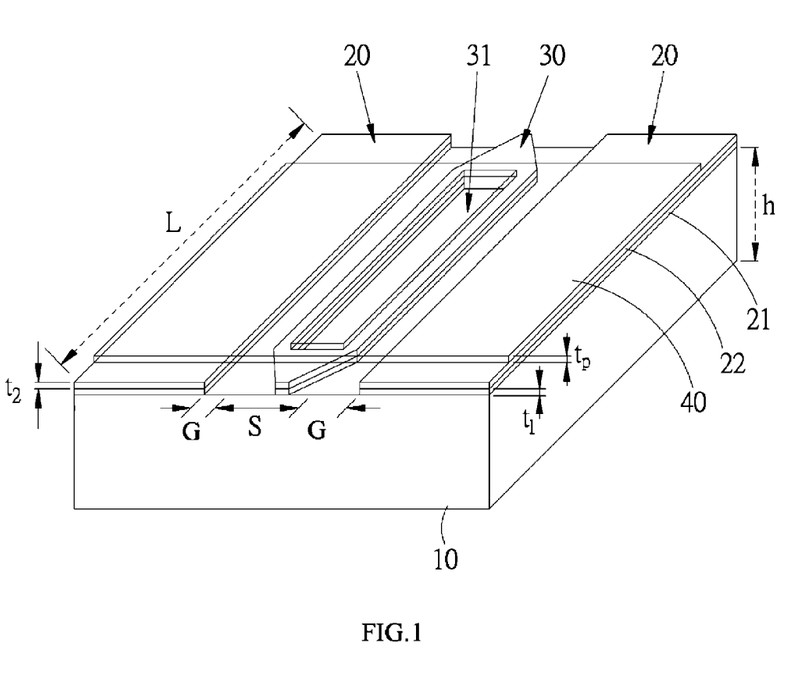
FIG. 1 is a structural schematic diagram of a preferred embodiment of a biosensor chip having precise count function of the present invention.

Please refer to FIG. 1 which is a structural schematic diagram of a preferred embodiment of a biosensor chip having precise count function of the present invention. The biosensor chip having precise count function of the present invention at least comprises a substrate 10, a plurality of ground wire waveguide layers 20, a signal waveguide layer 30 and a protective layer 40.

The substrate 10 is formed of such as a glass substrate, wherein the size of the glass substrate is such as about 60×60×0.7 mm$^3$.

The ground wire waveguide layers 20 are located on two sides of the substrate 10, and the ground wire waveguide layers 20 is formed by stacking such as a first metal layer 21 and a second metal layer 22. Wherein, the first metal layer 21 and the second metal layer 22 are formed of Ni, Cr, Ti or Au, respectively; wherein, preferably, the first metal layer 21 is Ti and has a thickness $t_1$ such as about 1.5 μm; and the second metal layer 22 is preferably Au and has a thickness $t_2$ such as about 0.5 μm.

The signal waveguide layer 30 is located on the substrate 10 and between the ground wire waveguide layers 20. Wherein the signal waveguide layer 30 has a cell sensing region formed of a recess 31 having a size of such as 3000×600 μm$^2$ to inject cell and/or culture medium for the follow-up measurement. The signal waveguide layer 30 is also formed by stacking such as the first metal layer 21 and the second metal layer 22, wherein the first metal layer 21 and the second metal layer 22 are formed of such as Ni, Cr, Ti or Au, respectively, and wherein, preferably, the first metal layer 21 is Ti and has a thickness $t_1$ such as about 1.5 μm; and the second metal layer 22 is preferably Au and has a thickness $t_2$ such as about 0.5 μm.

The protective layer 40 covers a portion of the ground wire waveguide layers 20 and a portion of the signal waveguide layer 30 to expose the recess 31, wherein, the protective layer 40 is formed of SU-8 photoresist (from MicroChem Corporation or Hexion Specialty Chemicals) and has a thickness $t_p$ such as 55 μm, and the recess 31 has a depth of about 57 μm.

Therefore, the biosensor chip having precise count function of the present invention not only can measure amount of cells precisely by the cell sensing region formed of the recess 31 of the signal waveguide layer 30, but also cover frequency band between 1 GHz and 40 GHz so as to provide the continuous frequency response.

Although the preceding description has explicitly explained the system schematic diagram of a preferred embodiment of the biosensor chip having precise count function of the present invention. For the sake of accuracy, hereinafter will elaborate it in detail with the other flow charts of manufacturing process. The illustrations are only used as examples, but shall not subject to this restriction.

Figure 2:
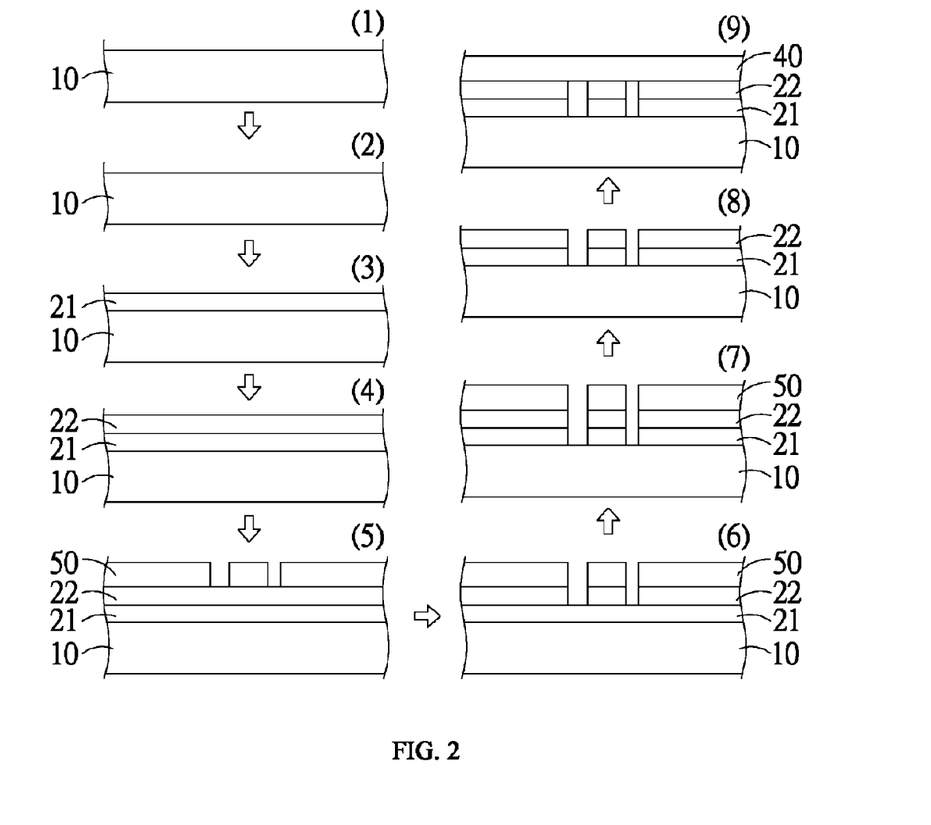
FIG. 2 is a front view diagram of manufacturing process of a preferred embodiment of a biosensor chip having precise count function as shown in FIG. 1.

Please refer to FIG. 2 which is a front view diagram of manufacturing process of a preferred embodiment of a biosensor chip having precise count function as shown in FIG. 1. Step (1) is to provide the substrate 10, and the following step (2) is to conduct RCA Clean to the substrate 10 to remove various pollutions thereon.

Step (3) is to dispose the first metal layer 21 of 1.5 μm thickness on the substrate 10 by using Ti metal target via RF magnetron sputtering under the condition of argon atmosphere.

Step (4) is to dispose the second metal layer 22 of 0.5 μm thickness on the first metal layer 21 by using gold foil via E-beam evaporation. It is worthy to mention that as gold is of excellent electrical characteristic and biocompatibility, it is therefore applicable to be the material of the second metal layer 2 applied to the biosensor chip of the present invention.

Step (5) is to define the structure of the biosensor chip of the present invention by AZ5214E photo mask, and sequentially, steps (6) and (7) are to remove a portion of the first metal layer 21 and the second metal layer 22 by wet etching process, and step (8) is to remove the photoresist 50 by acetone.

Step (9) is to cover the protective layer 40 of about 55 μm thickness on the second metal layer 22 so as to obtain the biosensor chip having precise count function of the present invention. Wherein, the protective layer 40 is formed of such as SU-8 photoresist. It is noticeable that as cell is hard to adhere to SU-8 photoresist; it is therefore suitable for serving as the material of the protective layer 40 of the biosensor chip of the present invention.

Figure 3:
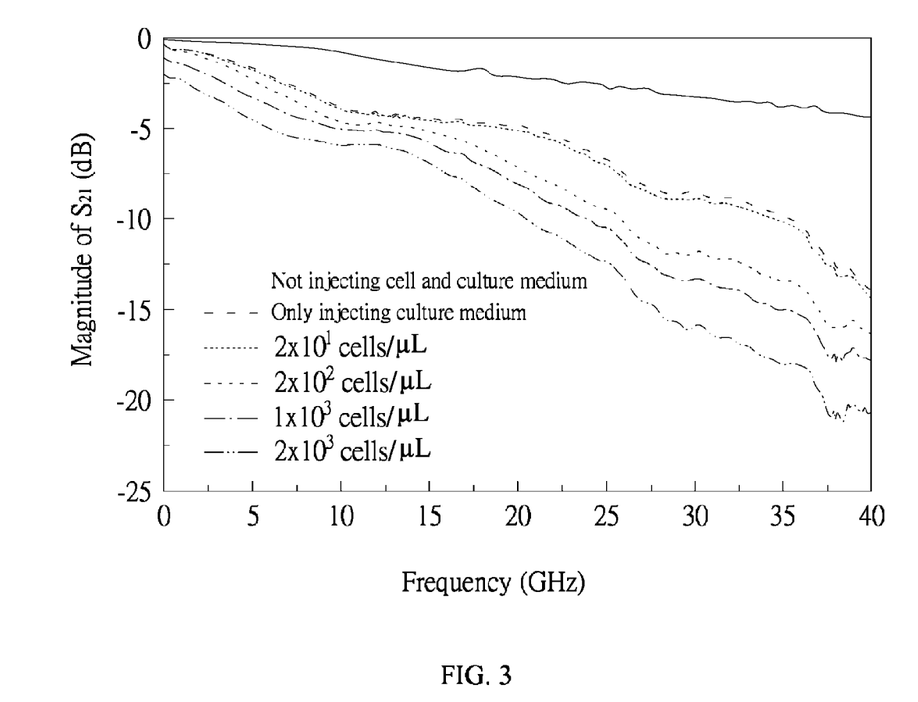
FIG. 3 is a scattering parameter diagram obtained by measuring a biosensor chip having precise count function of the present invention.

Please refer to FIG. 3 which is a scattering parameter diagram obtained by measuring a biosensor chip having precise count function of the present invention.

Take human hepatoma cells (HepG2) for example, HepG2 cells is cultured in DMEM containing fetal bovine serum of 10%, penicillin of 100 unit/ml, streptomycin of 100 μg/ml, $NaHCO_3$ of 0.3% (w/v), non-essential amino acid of 0.1 mM and sodium pyruvate of 1 mM, and has to be maintained in 37° C. in $CO_2$ of 5%.

Sequentially, injecting the HepG2 cells having different densities ($2\times10^1$ cells/μL, $2\times10^2$ cells/μL, $1\times10^3$ cells/μL and $2\times10^3$ cells/μL) and the culture medium into the cell sensing region of the biosensor chip of the present invention, and measuring the scattering parameter $S_{21}$ by Agilent N5247 vector network analyzer. In addition, the present invention further measures the scattering parameter $S_{21}$ which is not injected the HepG2 cells and the culture medium, but only injects the culture medium.

As can be seen in FIG. 3, when the density of HepG2 cells is higher, magnitude of the scattering parameter $S_{21}$ is therefore decreased. This is because of the microwave attenuation caused by electromagnetic wave penetrating the HepG2 cells, and the influence is more obvious than polarization effects. Therefore, when the cell sensing region is contained cells, without cells and of different cell densities, the frequency response will cause bias, and according to the amount of the bias, it can further calculate the equivalent RLGC value, attenuation constant α(f) and dielectric constant $\in_r(f)$ of the HepG2 cells. Wherein, the scattering parameter of the HepG2 cells satisfies with the following relations:

$$\begin{bmatrix} S_{11} & S_{12} \\ S_{21} & S_{22} \end{bmatrix}_{cell} = \begin{bmatrix} S_{11} & S_{12} \\ S_{21} & S_{22} \end{bmatrix}_{loaded} - \begin{bmatrix} S_{11} & S_{12} \\ S_{21} & S_{22} \end{bmatrix}_{medium} - \begin{bmatrix} S_{11} & S_{12} \\ S_{21} & S_{22} \end{bmatrix}_{unloaded}, \quad (a)$$

and wherein, $$\begin{bmatrix} S_{11} & S_{12} \\ S_{21} & S_{22} \end{bmatrix}_{loaded}$$

is a loaded scattering parameter obtained by measuring the biosensor chip injecting the HepG2 cells and the culture medium;

$$\begin{bmatrix} S_{11} & S_{12} \\ S_{21} & S_{22} \end{bmatrix}_{medium}$$

is a medium scattering parameter obtained by measuring the biosensor chip only injecting the culture medium; and $$\begin{bmatrix} S_{11} & S_{12} \\ S_{21} & S_{22} \end{bmatrix}_{unloaded}$$

is an unloaded scattering parameter obtained by measuring the biosensor chip not injecting the HepG2 cells and the culture medium.

Sequentially, using the relation (a) can infer a propagation constant γ(f)=α(f)+jβ(f), wherein α(f) is an attenuation constant and β(f) is a phase constant, and is respectively $$\alpha(f) = 8.686 \cdot \left[ -\frac{1}{L} \text{Re} \left\{ \ln \left[ \frac{1 - S_{11}^2 + S_{21}^2}{2 S_{21}} \pm \left[ \frac{(S_{11}^2 - S_{21}^2 + 1)^2 - (2 S_{11})^2}{(2 S_{21})^2} \right]^{1/2} \right]^{-1} \right\} \right] \quad (b)$$

(dB/μm),

-continued $$\beta(f) = -\frac{1}{L}\text{Im}\left\{\ln\left[\frac{1-S_{11}^2+S_{21}^2}{2S_{21}} \pm \left[\frac{(S_{11}^2-S_{21}^2+1)^2-(2S_{11})^2}{(2S_{21})^2}\right]^{1/2}\right]^{-1}\right\} = \quad (c)$$

$$\frac{2\pi \cdot f\sqrt{\varepsilon_{\text{eff}}(f)}}{c} \text{(rad/}\mu\text{m)}.$$

Wherein, L is a length of the signal waveguide layer and is 6600 μm in the embodiment; $\in_{\text{eff}}(f)$ is an effective dielectric constant; f is a frequency, and c is light velocity of $3\times10^8$ m/s.

Accordingly, via the relation (c) it can obtain an effective dielectric constant $$\varepsilon_{\text{eff}}(f), \varepsilon_{\text{eff}}(f) = 1 + \frac{\varepsilon_r(f)-1}{2} \cdot \frac{K(k_1)}{K(k_1')} \cdot \frac{K(k_0')}{K(k_0)} (d),$$

and can further obtain a characteristic impedance $Z_0(f)$ by the effective dielectric constant $$\varepsilon_{\text{eff}}(f), Z_0(f) = \frac{30\pi}{\sqrt{\varepsilon_{\text{eff}}(f)}} \frac{K(k_0')}{K(k_0)} (\Omega)(e),$$

and wherein $\in_r(f)$ is an dielectric constant; K(x) is an elliptical integral of a first kind;

$$k_0 = \frac{S}{S+2G}; k_1 = \frac{\sinh(\pi S/4h)}{\sinh(\pi(S+2G)/4h)}; k_i' = \sqrt{1-k_i^2} \ (i=0,1);$$

s is a width of the signal waveguide layer; G is an interval between the ground wire waveguide layer and the signal waveguide layer; and h is a thickness of the substrate.

Figure 4A:
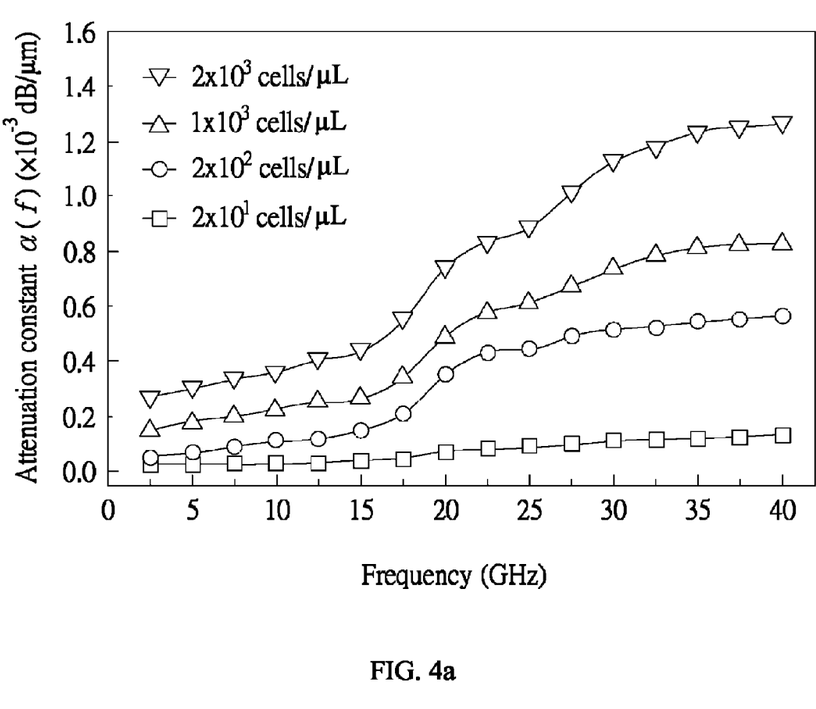
FIG. 4a is a cell-based attenuation constant diagram obtained by a method of sensing cell of the present invention.
Figure 4B:
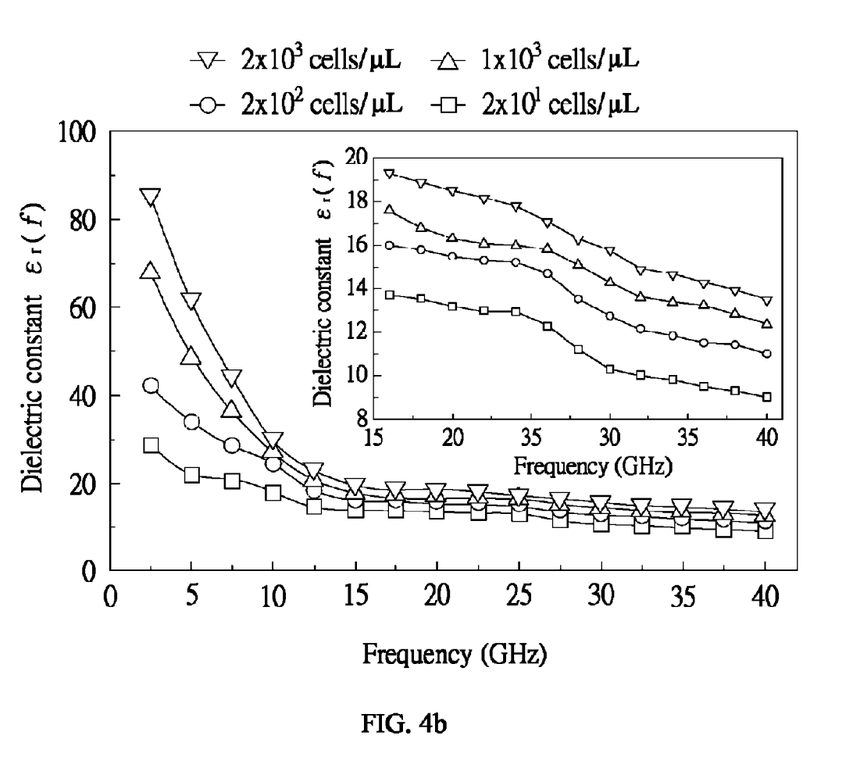
FIG. 4b is a cell-based dielectric constant diagram obtained by a method of sensing cell of the present invention.

Please refer to FIGS. 4a and 4b which are a cell-based attenuation constant diagram obtained by a method of sensing cell of the present invention and a cell-based dielectric constant diagram obtained by a method of sensing cell of the present invention, respectively.

Because the scattering parameter of the relation (a) has deleted the microwave parasitic effect of the culture medium and the substrate, it can obtain pure dielectric property of the HepG2 cells. As FIG. 4a shows, when frequency is 40 GHz, the attenuation constant α(f) of the HepG2 cells having density of $2\times10^1$ cells/μL, $2\times10^2$ cells/μL, $1\times10^3$ cells/μL and $2\times10^3$ cells/μL are $0.12\times10^{-3}$ dB/μm, $0.58\times10^{-3}$ dB/μm, $0.81\times10^{-3}$ dB/μm and $1.26\times10^{-3}$ dB/μm, respectively. And as shown in FIG. 4b, when frequency is between 15 GHz and 40 GHz, average values of the effective dielectric constant $\in_r(f)$ of the HepG2 cells are 11.37, 13.58, 14.6 and 16.4, individually. Therefore, by removing the microwave parasitic effect of the culture medium and the substrate is capable of enhancing the sensitivity while measuring cells, and even if the density of cells is very low, it can count amount of cells precisely.

Figure 5:
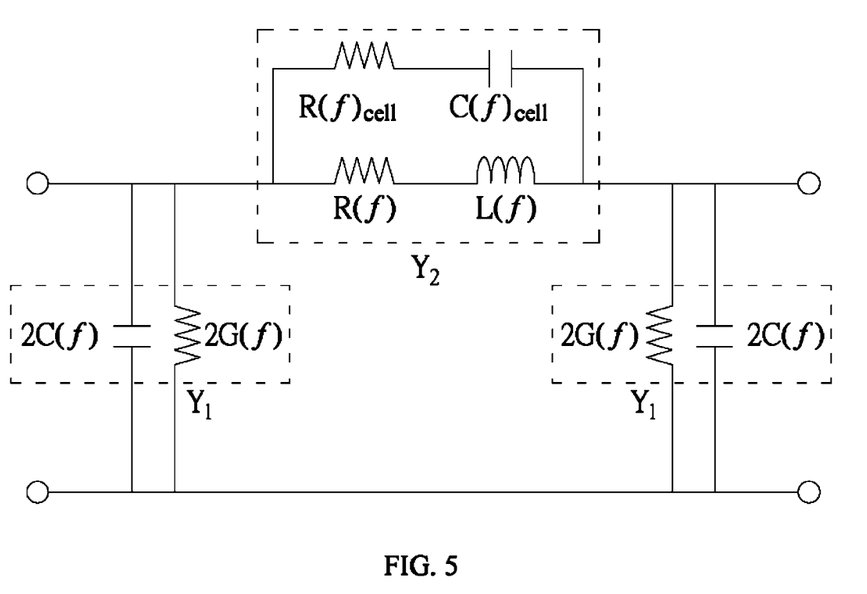
FIG. 5 is an equivalent circuit diagram of a preferred embodiment of a method of sensing cell of the present invention.
Figure 6A:
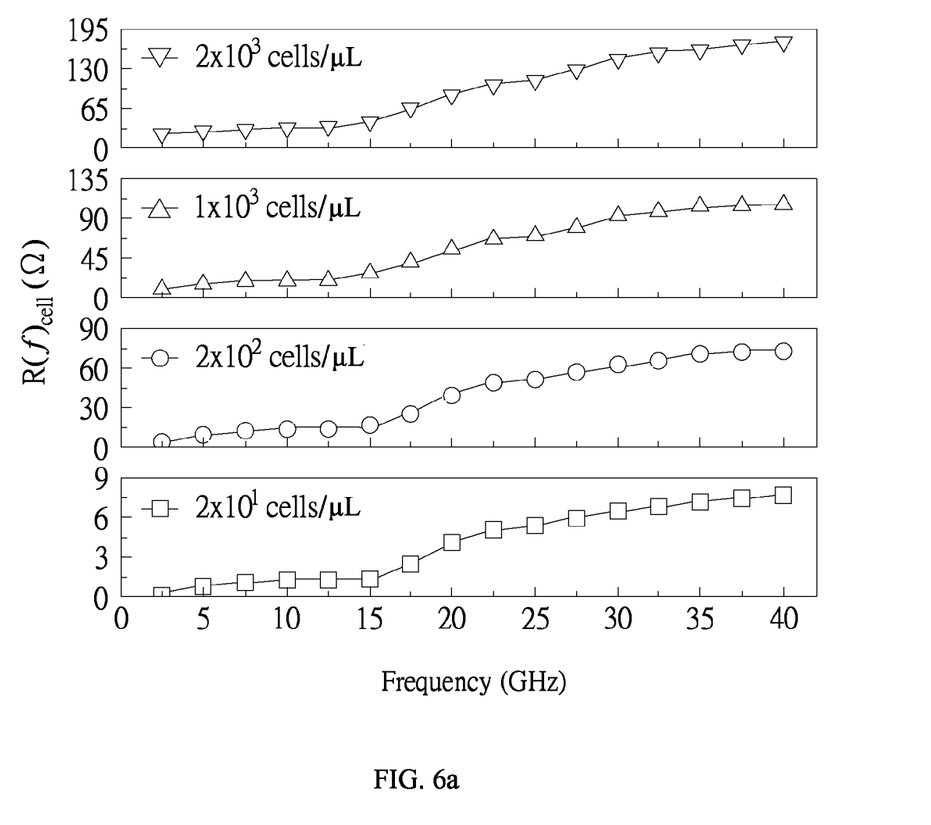
FIG. 6a is a cell equivalent resistance diagram obtained by a method of sensing cell of the present invention.
Figure 6B:
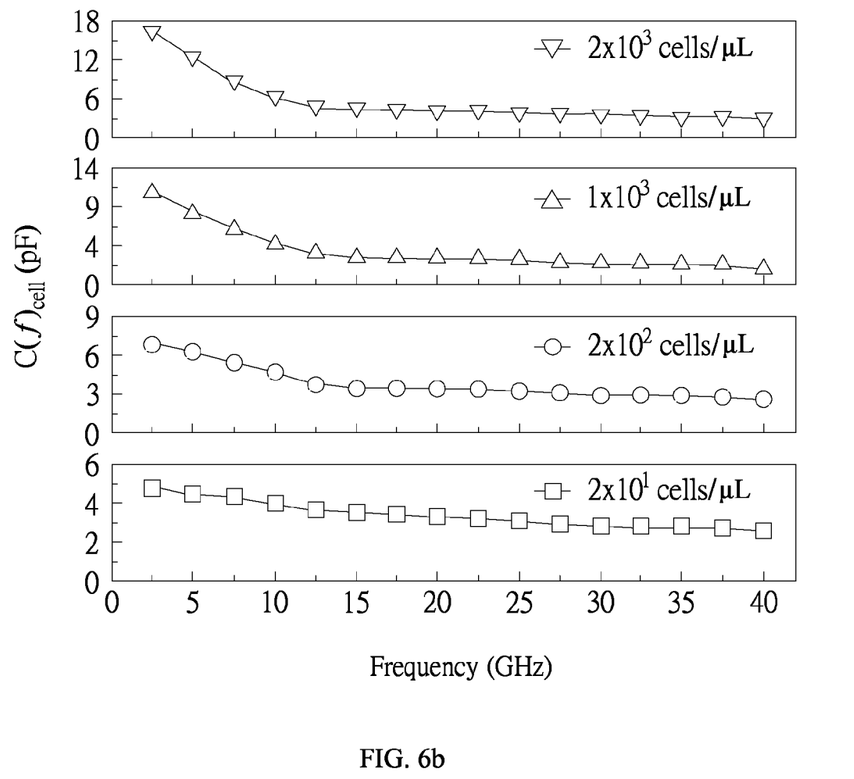
FIG. 6b is a cell equivalent capacitance diagram obtained by a method of sensing cell of the present invention.

Please refer to FIGS. 5, 6a and 6b which are an equivalent circuit diagram of a preferred embodiment of a method of sensing cell of the present invention, a cell equivalent resistance diagram obtained by a method of sensing cell of the present invention and a cell equivalent capacitance diagram obtained by a method of sensing cell of the present invention, respectively.

The present invention can further use the scatter parameter and the relations (f) and (g), $$\gamma(f)\times Z_0(f)=R(f)+j\omega\cdot L(f) \qquad (f), \text{ and}$$

$$\gamma(f)/Z_0(f)=G(f)+j\omega\cdot C(f) \qquad (g)$$

to obtain an equivalent resistance $R(f)_{cell}$ and an equivalent capacitance $C(f)_{cell}$ of the HepG2 cells, wherein R(f) is a resistance, L(f) is an inductance, G(f) is an conductance, C(f) is a capacitance and ω is an angular frequency.

Firstly, indicating the loaded scattering parameter $$\begin{bmatrix} S_{11} & S_{12} \\ S_{21} & S_{22} \end{bmatrix}_{loaded}$$

in form of $$\begin{bmatrix} A & B \\ C & D \end{bmatrix}_{loaded}, \text{ wherein}$$

$$A = \frac{(1+S_{11})(1-S_{22})+S_{12}S_{21}}{2S_{21}} = 1 + \frac{Y_1}{Y_2} (h)$$

$$B = Z_0(f)\frac{(1+S_{11})(1+S_{22})-S_{12}S_{21}}{2S_{21}} = \frac{1}{Y_2} (i)$$

$$C = \frac{1}{Z_0(f)}\frac{(1-S_{11})(1-S_{22})-S_{12}S_{21}}{2S_{21}} = 2Y_1 + \frac{Y_1^2}{Y_2} (j)$$

$$D = \frac{(1-S_{11})(1+S_{22})+S_{12}S_{21}}{2S_{21}} = 1 + \frac{Y_1}{Y_2} (k),$$

wherein, $Y_1$ is an equivalent circuit of the substrate, and $Y_2$ is an equivalent circuit of the culture medium and the HepG2 cells.

Sequentially, it can further obtain an equivalent resistance $R(f)_{cell}$ and an equivalent capacitance $C(f)_{cell}$ the HepG2 cells via the relations (f), (g) and (i), which are:

$$R(f)_{cell} = \frac{1}{\text{Re}[Y_2]} (l)$$

$$C(f)_{cell} = \text{Im}[Y_2](m),$$

Wherein, $$Y_2 = \frac{1}{R(f)+j\omega \cdot L(f)}\bigg|_{unloaded} + \frac{j\omega \cdot R(f)_{cell} \cdot C(f)_{cell}+1}{j\omega \cdot C(f)_{cell}}\bigg|_{cell}$$

$$= \frac{(1-\omega^2 \cdot L(f) \cdot C(f)_{cell}) + j\left(\begin{array}{c}\omega \cdot R(f)_{cell} \cdot C(f)_{cell} + \\ \omega \cdot R(f) \cdot C(f)_{cell}\end{array}\right)}{(R(f)-\omega^2 \cdot R(f)_{cell} \cdot C(f)_{cell}) + j\left(\begin{array}{c}\omega \cdot R(f) \cdot \\ R(f)_{cell}C(f)_{cell}+\omega \cdot L(f)\end{array}\right)}(n).$$

Consequently, the electrical characteristic of the HepG2 cells can be explicitly explained via the relations (l), (m) and (n). For an example as operating at 40 GHz, as can be seen in FIGS. 6a and 6b, when the density of the HepG2 cells is changed from $2\times10^1$ cells/μL to $2\times10^3$ cells/μL, the equivalent resistance $R(f)_{cell}$ of the HepG2 cells will increase from 8.7Ω to 177.9Ω, and the equivalent capacitance $C(f)_{cell}$ of the HepG2 cells will increase from 2.53 pF to 2.88 pF. In other words, by using the biosensor chip and method of sensing cell of the present invention, it can thereby effectively enhance the sensitivity while measuring the HepG2 cells and to obtain amount of the HepG2 cells more precisely so as to prevent carcinogenesis effectively.

While the means of specific embodiments in present invention has been described by reference drawings, numerous modifications and variations could be made thereto by those skilled in the art without departing from the scope and spirit of the invention set forth in the claims. The modifications and variations should in a range limited by the specification of the present invention.

What is claimed is:

1. A biosensor chip, comprising:
   a substrate;
   a plurality of ground wire waveguide layers located on two sides of the substrate;
   a signal waveguide layer located on the substrate and between the plurality of ground wire waveguide layers, wherein the signal waveguide layer defines a recess therein, the recess forming a cell sensing region wherein cells are injected and cultured; and
   a protective layer covering a portion of the ground wire waveguide layers and a portion of the signal waveguide layer to expose the recess.

2. The biosensor chip as defined in claim 1, wherein the ground wire waveguide layers and the signal waveguide layer are formed by stacking a first metal layer and a second metal layer.

3. The biosensor chip as defined in claim 2, wherein the first metal layer and the second Metal layer are formed of Ni, Cr, Ti or Au, respectively.

4. The biosensor chip as defined in claim 1, wherein the substrate is a glass substrate.

5. The biosensor chip as defined in claim 1, wherein the protective layer is formed of SU-8 photoresist.

6. The biosensor chip as defined in claim 1, wherein operating frequency hand of the biosensor chip having precise count function is between 1 GHz and 40 GHz.

* * * * *